United States Patent
Huang et al.

(10) Patent No.: US 11,873,515 B2
(45) Date of Patent: Jan. 16, 2024

(54) DEHYDROGENASE MUTANT L283V/L286V, AND PREPARATION METHOD AND USE THEREOF

(71) Applicants: GOLDEN HEALTH (GUANGDONG) BIOTECHNOLOGY CO., LTD., Foshan (CN); TF BIOSYN BIOTECHNOLOGY CO., LTD., Foshan (CN)

(72) Inventors: Jiajun Huang, Foshan (CN); Rongxu Li, Foshan (CN); Ziying Wu, Foshan (CN); Haoxuan Hu, Foshan (CN); Shaoyu Bai, Foshan (CN); David Zhou, Foshan (CN); Tony Lu, Foshan (CN)

(73) Assignees: GOLDEN HEALTH (GUANGDONG) BIOTECHNOLOGY CO., LTD., Foshan (CN); TF BIOSYN BIOTECHNOLOGY CO., LTD., Foshan (CN)

( * ) Notice: Subject to any disclaimer, the term of this patent is extended or adjusted under 35 U.S.C. 154(b) by 0 days.

(21) Appl. No.: 18/056,728

(22) Filed: Nov. 18, 2022

(65) Prior Publication Data

US 2023/0193217 A1 Jun. 22, 2023

(30) Foreign Application Priority Data

Nov. 18, 2021 (CN) .......................... 202111369684.9

(51) Int. Cl.
| | |
|---|---|
| *C12N 9/02* | (2006.01) |
| *C12N 15/70* | (2006.01) |
| *C12P 17/16* | (2006.01) |

(52) U.S. Cl.
CPC ........... *C12N 9/0008* (2013.01); *C12N 15/70* (2013.01); *C12P 17/165* (2013.01); *C12Y 102/04001* (2013.01)

(58) Field of Classification Search
None
See application file for complete search history.

(56) References Cited

U.S. PATENT DOCUMENTS

| | | | |
|---|---|---|---|
| 2014/0171380 A1 | 6/2014 | Kim et al. | |
| 2020/0157589 A1* | 5/2020 | Mccague | C12N 9/0028 |
| 2022/0154231 A1* | 5/2022 | Li | C12Y 101/01047 |

FOREIGN PATENT DOCUMENTS

| | | | |
|---|---|---|---|
| CN | 108559735 A | | 9/2018 |
| CN | 110592042 A | | 12/2019 |
| CN | 113373188 A | | 9/2021 |
| CN | 113801858 A | * | 12/2021 |
| JP | S5881791 A | | 5/1983 |
| WO | 2021113337 A1 | | 6/2021 |
| WO | WO-2021180019 A1 | * | 9/2021 |

\* cited by examiner

*Primary Examiner* — Todd M Epstein

(57) ABSTRACT

The present invention provides a dehydrogenase mutant L283V/L286V, and a preparation method and use thereof, and relates to the field of biomedicine technologies. An amino acid sequence of the mutant L283V/L286V is as shown in SEQ ID NO: 1; and the mutant is prepared by simultaneously mutating $283^{rd}$ and $286^{th}$ leucine of a dehydrogenase with an amino acid sequence as shown in SEQ ID NO: 3 into valine. The dehydrogenase mutant L283V/L286V shows high selectivity in catalyzing myosmine reduction reaction in a whole cell system to produce S-nornicotine, and has relatively high dehydrogenase and imine reductase activities, a short enzyme reduction time, and a high transformation rate. The product S-nornicotine obtained through the reaction has extremely high optical purity, which reduces the operation difficulty of subsequent purification.

8 Claims, 6 Drawing Sheets

Specification includes a Sequence Listing.

SEQUENCE LISTING

```
Sequence total quantity: 6
SEQ ID NO: 1                moltype = AA  length = 304
FEATURE                     Location/Qualifiers
source                      1..304
                            mol_type = protein
                            organism = synthetic construct
SEQUENCE: 1
MASNVCVLGA GRMGSSIART LLDRGYPTWV WNRTAAKCEP LAALGAKVAS SVQEGIQAAE    60
VVIINVLDYA ASDALLKRDG IASALAGKAV VQLTSGSPRL AREEARWVEA HGAGYLDGAI   120
MATPDFIGKP ETAMLYSGSR DVYEKHKPLL FALGGGTNYV GELPGQASAL DTALLTQMWG   180
GLFGALQGMA VAEAEGLDLE TFRNHLSAFK PVVDASLFDL VDRTNARRFA GDDATLASLG   240
AHYSAFQHLL EACEERGLDA AMPRAMDMIF RQALSLGSME DDVASVALLF RNGSPRQSRE   300
PANA                                                                304

SEQ ID NO: 2                moltype = DNA  length = 912
FEATURE                     Location/Qualifiers
source                      1..912
                            mol_type = other DNA
                            organism = synthetic construct
SEQUENCE: 2
atggcaagca acgtttgtgt tttaggggcg gggcgcatgg gtagcagcat tgcgcggacg    60
ctgttagacc gcgggtatcc gacctgggtt tggaatcgga cggcggcgaa atgtgaaccg   120
ttagcagcac tgggtgcgaa agttgcatct agtgttcagg aaggaatcca agcagcagaa   180
gttgttatca taaacgttct ggattatgcg gcaagcgacg cactgctgaa aagagatggc   240
atagcaagcg cactggcagg taaagcagtt gtgcaactga caagcggtag cccgcgtctg   300
gcacgggaag aagcacgttg ggtggaagca catggagcag gctatctgga tggagcaatt   360
atggcaacac cagattttat tggaaaaccg gaaacagcaa tgctgtatag cggtagcaga   420
gatgtgtatg agaaacataa accgttatta ttcgcactgg gtggtggaac aaattatgtg   480
ggtgaactgc cgggccaggc aagcgcatta gataccgccc tgctgacaca gatgtggggt   540
gggctgtttg gtgcactgca ggggatggca gttgcagaag cagaaggcct ggatctggag   600
acctttcgta atcacctgtc agcatttaag ccggttgttg acgcgagcct gtttgattta   660
gttgatcgta ccaatgcacg tcggtttgcg ggtgatgatg caacattagc aagcctgggc   720
gcccattatt ccgcctttca gcatctgtta gaggcatgtg aagaacgtgg tctggatgcg   780
gcaatgccgc gtgcaatgga tatgattttt cgtcaggcac tgagcctggg aagcatggaa   840
gacgatgttg caagcgttgc attactgttt cgtaatggta gtcctcgtca aagcagagaa   900
ccggcaaatg ca                                                       912

SEQ ID NO: 3                moltype = AA  length = 304
FEATURE                     Location/Qualifiers
source                      1..304
                            mol_type = protein
                            organism = synthetic construct
SEQUENCE: 3
MASNVCVLGA GRMGSSIART LLDRGYPTWV WNRTAAKCEP LAALGAKVAS SVQEGIQAAE    60
VVIINVLDYA ASDALLKRDG IASALAGKAV VQLTSGSPRL AREEARWVEA HGAGYLDGAI   120
MATPDFIGKP ETAMLYSGSR DVYEKHKPLL FALGGGTNYV GELPGQASAL DTALLTQMWG   180
GLFGALQGMA VAEAEGLDLE TFRNHLSAFK PVVDASLFDL VDRTNARRFA GDDATLASLG   240
AHYSAFQHLL EACEERGLDA AMPRAMDMIF RQALSLGSME DDLASLALLF RNGSPRQSRE   300
PANA                                                                304

SEQ ID NO: 4                moltype = DNA  length = 912
FEATURE                     Location/Qualifiers
source                      1..912
                            mol_type = other DNA
                            organism = synthetic construct
SEQUENCE: 4
atggcaagca acgtttgtgt tttaggggcg gggcgcatgg gtagcagcat tgcgcggacg    60
ctgttagacc gcgggtatcc gacctgggtt tggaatcgga cggcggcgaa atgtgaaccg   120
ttagcagcac tgggtgcgaa agttgcatct agtgttcagg aaggaatcca agcagcagaa   180
gttgttatca taaacgttct ggattatgcg gcaagcgacg cactgctgaa aagagatggc   240
atagcaagcg cactggcagg taaagcagtt gtgcaactga caagcggtag cccgcgtctg   300
gcacgggaag aagcacgttg ggtggaagca catggagcag gctatctgga tggagcaatt   360
atggcaacac cagattttat tggaaaaccg gaaacagcaa tgctgtatag cggtagcaga   420
gatgtgtatg agaaacataa accgttatta ttcgcactgg gtggtggaac aaattatgtg   480
ggtgaactgc cgggccaggc aagcgcatta gataccgccc tgctgacaca gatgtggggt   540
gggctgtttg gtgcactgca ggggatggca gttgcagaag cagaaggcct ggatctggag   600
acctttcgta atcacctgtc agcatttaag ccggttgttg acgcgagcct gtttgattta   660
gttgatcgta ccaatgcacg tcggtttgcg ggtgatgatg caacattagc aagcctgggc   720
gcccattatt ccgcctttca gcatctgtta gaggcatgtg aagaacgtgg tctggatgcg   780
gcaatgccgc gtgcaatgga tatgattttt cgtcaggcac tgagcctggg aagcatggaa   840
gacgatctgg caagcttagc attactgttt cgtaatggta gtcctcgtca aagcagagaa   900
ccggcaaatg ca                                                       912

SEQ ID NO: 5                moltype = DNA  length = 33
FEATURE                     Location/Qualifiers
source                      1..33
                            mol_type = other DNA
                            organism = synthetic construct
```

```
SEQUENCE: 5
gatgttgcaa gcgttgcatt actgtttcgt aat                              33

SEQ ID NO: 6              moltype = DNA  length = 33
FEATURE                   Location/Qualifiers
source                    1..33
                          mol_type = other DNA
                          organism = synthetic construct
SEQUENCE: 6
tgcaacgctt gcaacatcgt cttccatgct tcc                              33
```

DEHYDROGENASE MUTANT L283V/L286V, AND PREPARATION METHOD AND USE THEREOF

STATEMENT REGARDING SEQUENCE LISTING

The instant application contains a Sequence Listing which has been submitted electronically in ST.26 format on Nov. 18, 2022, and was incorporated by reference in its entirety. Said ST.26 copy, created on Nov. 18, 2022, was named 1US0160JILY22-sequence-listing.xml and was 8,838 bytes in size.

TECHNICAL FIELD

The present invention relates to the field of biomedicine technologies, and in particular, to a dehydrogenase mutant L283V/L286V, and a preparation method and use thereof.

BACKGROUND

Nicotine is an alkaloid held in Solanaceae plant tobacco, accounting for 95% or more of all alkaloids in tobacco. The nicotine with a chemical name of 1-methyl(2-pyridyl)pyrrolidine and a molecular formula of C10H14N2 is an organic binary weak base with strong alkalinity, can form single or double crystalline salts with various inorganic or organic acids, and exists mostly in the form of organic salts in tobacco leaves.

The nicotine has a very wide use range. Nicotine series pesticides are botanical insecticides, which are widely used for crops such as grain, oil plants, vegetables, fruits, and forage because the nicotine series pesticides have functions of vaporization, stomach toxicity, and contact toxicity and feature rapid degradation without residue, and the like. The nicotine series pesticides are ideal efficient pesticides and biological pesticides for producing green food. The nicotine is further widely used in the pharmaceutical industry, and is a special raw material for developing drugs for treating diseases such as cardiovascular diseases, skin diseases, and snake venom. In clinical research, the nicotine further plays an active role in preventing and treating Alzheimer's disease (AD) and Parkinson's disease (PD). Some experimental and clinical results show that the nicotine can affect a degree of changes in neurofibrillary tangles in AD, and can improve cognitive impairment of AD patients through subcutaneous and intravenous administration, especially an information processing ability and a short-term memory ability.

At present, natural nicotine (S-nicotine) used in the market is obtained mainly depending on extraction from plants, including microwave extraction, ultrasonic extraction, supercritical extraction, and the like. However, the method of extraction from plants is inefficient, and because of the influence of raw materials, climate, growth cycle, and the like, tobacco-specific nicotine-related impurities are also contained during nicotine extraction. Long-term use of such impurities will cause potential harm to health. The nicotine obtained through extraction from plants still needs to undergo a series of purification steps before high-purity S-nicotine can be obtained. Therefore, much attention has been paid to a preparation method for high-efficiency synthesis of high-purity S-nicotine.

S-nornicotine is an important precursor for synthesis of S-nicotine. S-nornicotine only needs to undergo one-step methylation reaction and then S-nicotine can be generated, and S-nornicotine with high optical purity is the guarantee for the synthesis of high-purity S-nicotine.

An enzyme is a biocatalyst produced by living cells, which has high specificity and high catalytic efficiency for a substrate thereof. The high efficiency and specificity of the enzyme make the enzyme widely used in the synthesis of high-purity compounds. With the gradual maturity of molecular biology, protein engineering and other related technologies, interpretation methods of an enzyme catalytic mechanism and design techniques of enzymes are becoming increasingly abundant. It is a direction worthy of research to complete the synthesis of S-nornicotine with high optical purity by using a biological enzyme method. The rational design of protein engineering is to purposefully design and transform protein with a site-directed mutagenesis technology as main means and based on the understanding of a relationship between the structure and functions of proteins, so that performance of the proteins can achieve a desired effect. At present, in a large number of studies, the rational design technique has been used to successfully modify the catalytic activity, substrate specificity, thermal stability, an enzymatic allosteric effect, and the like of natural enzymes. With the development of computational biology, a method of using a computer aided design to guide enzyme modification is becoming increasingly mature. A computer simulation method is used to establish a three-dimensional structure model of an enzyme, analyze a conformational relationship between the enzyme and a substrate, quickly locate a region related to catalytic reaction, reduce a mutagenesis library capacity, and efficiently obtain relevant targets, which provides guidance for protein engineering transformation. However, at present, there is no relevant research on the design and modification of an enzyme by using protein engineering to complete the synthesis of S-nornicotine with high optical purity by using a biological enzyme method.

SUMMARY

To overcome the shortcomings of the prior art, a first objective of the present invention is to design and provide a dehydrogenase mutant L283V/L286V, which is used to prepare S-nornicotine, with a rich substrate diversity, high optical purity of the product, a short enzymolysis time, and a high transformation rate.

A second objective of the present invention is to provide a preparation method for the foregoing dehydrogenase mutant L283V/L286V, which is used to prepare the dehydrogenase mutant L283V/L286V by using a site-directed mutagenesis technology, with high stability.

A third objective of the present invention is to provide use of the foregoing dehydrogenase mutant L283V/L286V in preparation of S-nornicotine with high optical purity.

The first objective of the present invention is achieved by using the following technical solution:

A dehydrogenase mutant L283V/L286V is provided, where an amino acid sequence of the dehydrogenase mutant L283V/L286V is as shown in SEQ ID NO: 1.

Further, a nucleotide sequence of a gene encoding the mutant L283V/L286V is as shown in SEQ ID NO: 2.

Further, the mutant L283V/L286V is prepared by simultaneously mutating $283^{rd}$ and $286^{th}$ leucine of an MesPDH enzyme with an amino acid sequence as shown in SEQ ID NO: 3 into valine.

The second objective of the present invention is achieved by using the following technical solution:

A preparation method for the dehydrogenase mutant L283V/L286V includes the following steps:

S1: ligating an MesPDH enzyme gene into a plasmid to obtain a recombinant plasmid;

S2: designing a mutation primer, performing PCR amplification by using the mutation primer and with the recombinant plasmid as a template, so that $283^{rd}$ and $286^{th}$ amino acids of the MesPDH enzyme are simultaneously mutated into valine, and after the template DNA is removed through enzyme digestion, obtaining a mutant product through recovery; and S3: transforming the mutant product into a host cell, culturing to obtain a dehydrogenase mutant L283V/L286V expression strain, and inducing expression to obtain a dehydrogenase mutant L283V/L286V.

Further, a nucleotide sequence of the MesPDH enzyme gene is as shown in SEQ ID NO: 4.

Further, the mutation primer includes a primer 283/286-F and a primer 283/286-R; a sequence of the primer 283/286-F is as shown in SEQ ID NO: 5; and a sequence of the primer 283/286-R is as shown in SEQ ID NO: 6.

Further, the host cell is *Escherichia coli*.

Further, in step S2, reaction conditions of a PCR amplification procedure are as follows: pre-denaturation is performed at 98° C. for 3 min; and then a cycle is set to: denaturing at 98° C. for 10 s, annealing at 62° C. for 15 s, and extending at 72° C. for 2 min; and after 30 cycles, extension is performed at 72° C. for 10 min.

Use of the dehydrogenase mutant L283V/L286V in preparation of S-nornicotine with high optical purity is provided.

Further, the dehydrogenase mutant L283V/L286V is used to specifically reduce myosmine to prepare S-nornicotine with high optical purity.

Compared with the prior art, the present invention has the following beneficial effects:

The dehydrogenase mutant L283V/L286V according to the present invention is constructed by simultaneously mutating $283^{rd}$ and $286^{th}$ amino acids of an MesPDH enzyme into valine by using a site-directed mutagenesis technology, and can specifically reduce, by combining with a coenzyme circulating system in a whole cell organism, myosmine to prepare S-nornicotine with high optical purity, with a short enzymolysis time and a high transformation rate. The $283^{rd}$ leucine (L283) and the $286^{th}$ leucine (L286) of the dehydrogenase MesPDH are located in an active pocket, near the surface of the enzyme. Through molecular docking with myosmine, glucose, gluconic acid, NAD+, and NADH, these two amino acids are located in a region near myosmine, glucose and gluconic acid and slightly away from NAD+ and NADH. In the present invention, by mutating these two key amino acids into valine, compared with leucine, a side chain group of valine is shortened by one methylene group, thus expanding an active pocket space and increasing the diversity of substrates. In addition, the introduction of valine on the enzyme molecule surface helps to increase rigidity of the enzyme surface. The dehydrogenase activity of the mutant in preparation of S-nornicotine in a whole cell is improved, and the reductase activity and chiral selectivity are not affected.

In the preparation method for the dehydrogenase mutant L283V/L286V according to the present invention, site-directed mutation of the MesPDH enzyme is performed to construct the dehydrogenase mutant L283V/L286V, so that the catalytic activity of a specific substrate thereof is improved.

In the use of the dehydrogenase mutant in preparation of S-nornicotine in a whole-cell catalytic system according to the present invention, the dehydrogenase mutant is used to catalyze the preparation of S-nornicotine, which reduces reactant components in the reaction and makes the reaction system simpler and more convenient, and the optical purity of the product is high.

DESCRIPTION OF EMBODIMENTS

The present invention is further described below with reference to the accompanying drawings and specific implementations. It should be noted that the embodiments or technical features described below can be arbitrarily combined to form new embodiments provided that no conflict occurs. The following provides specific embodiments of the present invention, and the raw materials, equipment and the like used in the following embodiments can be obtained by purchasing, unless otherwise specified.

In the following embodiments, experimental methods with indicated specific conditions are provided, usually based on conventional experimental conditions or experimental conditions suggested by manufacturers. Unless otherwise specified, various reaction reagents involved in the embodiments can be purchased through commercial channels. For the experimental methods of molecular biology not specifically described in this embodiment, references may be made to the Molecular Cloning: A Laboratory Manual.

Embodiment 1

Figure 1A:
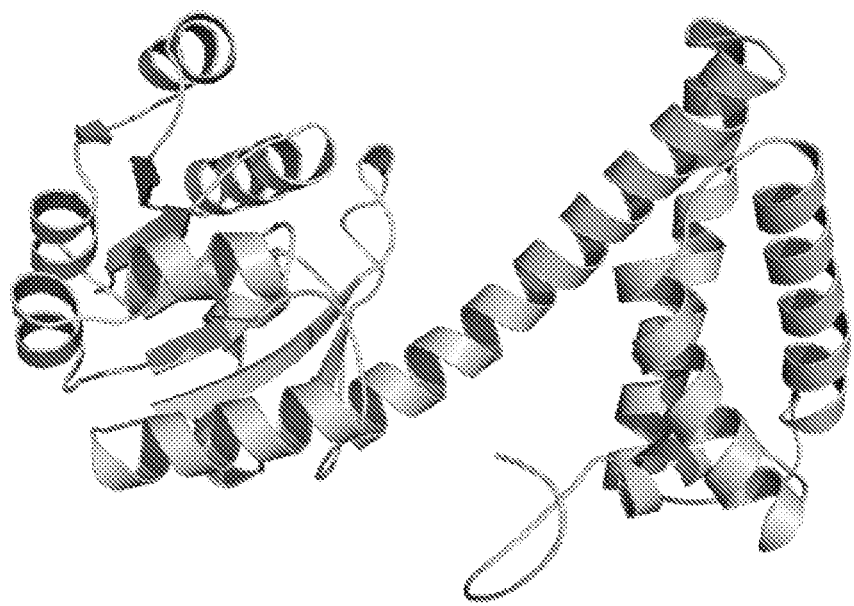
FIG. 1*a* is a three-dimensional structure diagram of a monomer MesPDH enzyme model Ma in Embodiment 1 of the present invention.

Establishment of a Tertiary Structure Model of an MesPDH Enzyme:

1. 6-phosphogluconate dehydrogenase MesPDH from *Mesorhizobium* sp. L48C026A00 was analyzed, a homologous modeling tool MODELLER was used to perform homologous modeling on MesPDH to obtain a monomer MesPDH enzyme model Ma, the model was evaluated, a Ramachandran diagram showed that all amino acids were in a reasonable region, and the proportion of amino acids in the best region was as high as 97.3%. The model is reasonable, and the model Ma is shown in FIG. 1*a*.

Figure 1B:
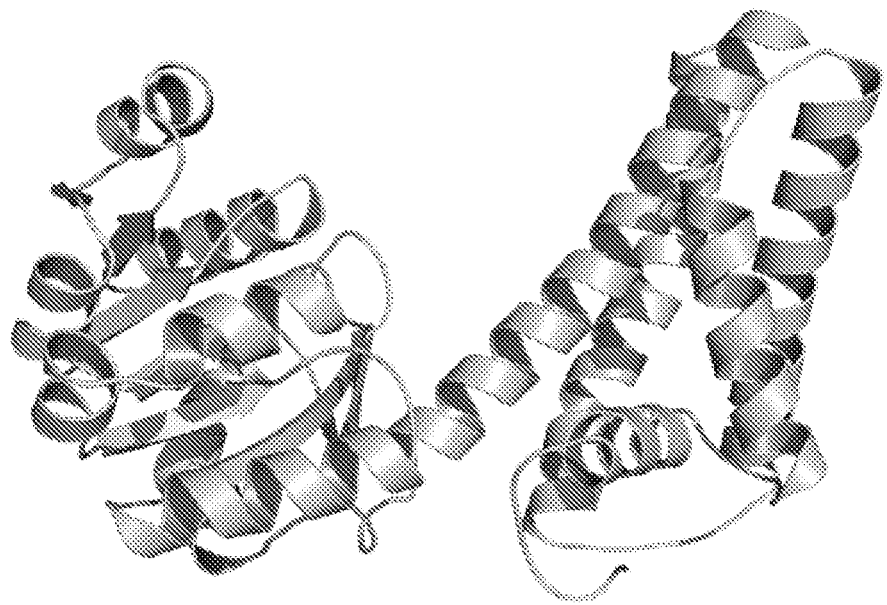
FIG. 1*b* is a three-dimensional structure diagram of a dimer MesPDH enzyme model Mb in Embodiment 1 of the present invention.

2. Swiss-model, an online homologous modeling tool, was used to perform homologous modeling on MesPDH to obtain a dimer MesPDH enzyme model Mb, the model was evaluated, a Ramachandran diagram showed that all amino acids were in a reasonable region, and the proportion of amino acids in the best region was as high as 94.6%. The model is reasonable, and the model Mb is shown in FIG. 1B.

Figure 1C:
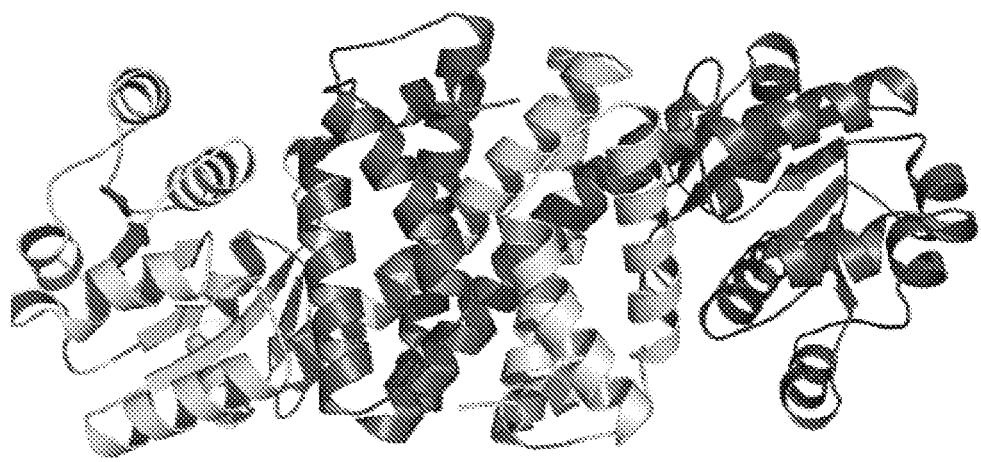
FIG. 1*c* is a three-dimensional structure diagram of a monomer MesPDH enzyme model Mc in Embodiment 1 of the present invention.

3. RoseTTAFold, an online modeling tool, was used to perform model prediction on MesPDH to obtain a monomer MesPDH enzyme model Mc, the model was evaluated, a Ramachandran diagram showed that all amino acids were in a reasonable region, and the proportion of amino acids in the best region was as high as 96.2%. The model is reasonable, and the model Mc is shown in FIG. 1c.

Embodiment 2

Molecular docking simulation was used to predict a binding conformation of each substrate and an enzyme and sites were selected.

1. Molecular Docking Simulation

Molecular simulation software Discovery Studio was used to locate active pocket centers of three modeling models, and molecular docking software AutodockVina was used to dock the MesPDH enzyme with myosmine, glucose, gluconic acid, NAD+, and NADH. A protein conformation analysis tool PyMOL was used to analyze each docking complex.

2. Docking Result Analysis

Figure 2A:
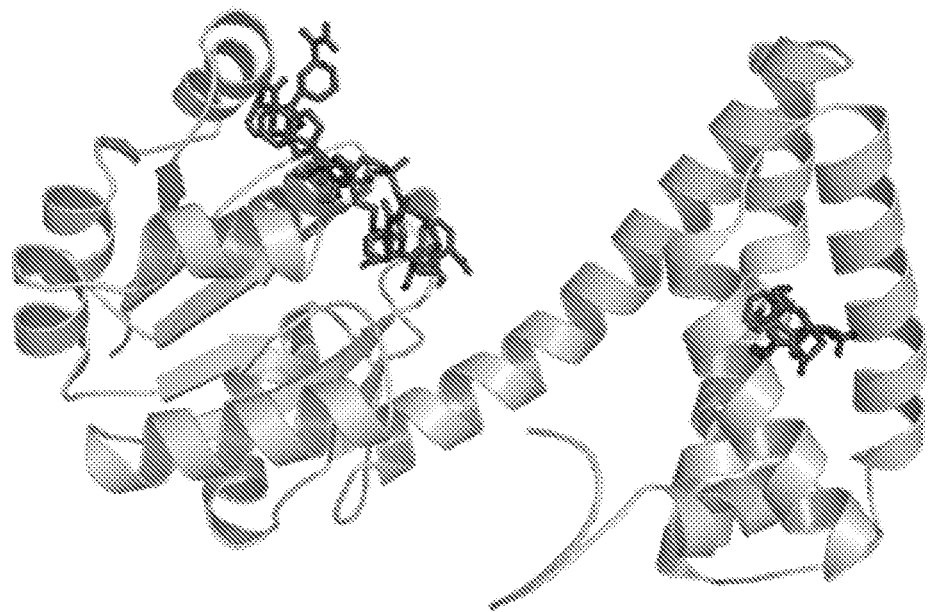
FIG. 2*a* is a simulation diagram of docking between a monomer MesPDH enzyme model Ma and different substrates in Embodiment 2 of the present invention.
Figure 2B:
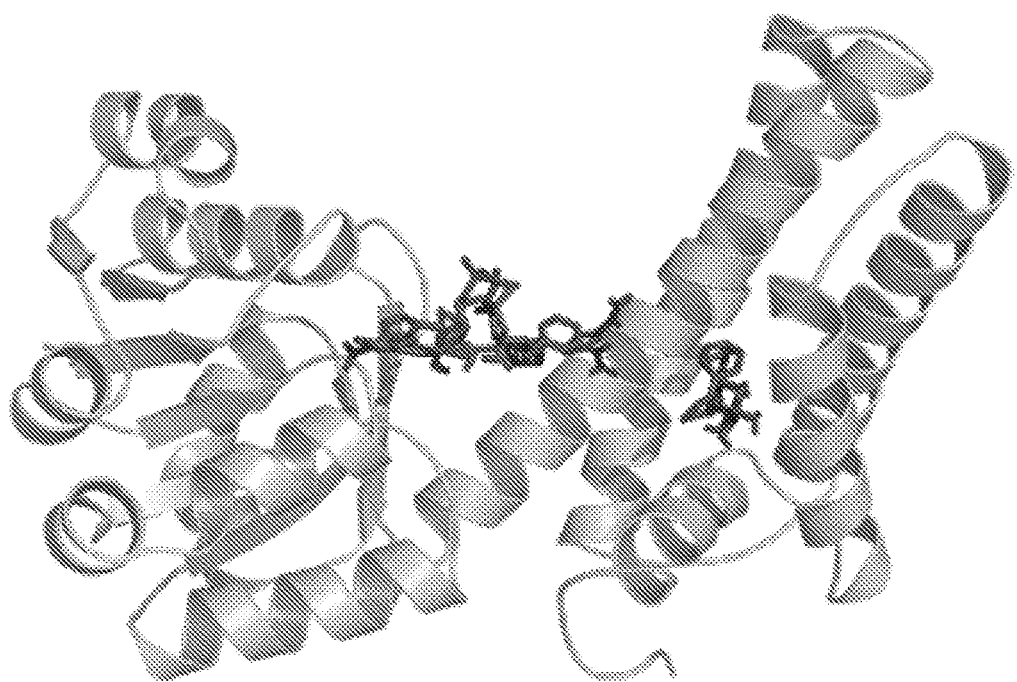
FIG. 2*b* is a simulation diagram of docking between a dimer MesPDH enzyme model Mb and different substrates in Embodiment 2 of the present invention.
Figure 2C:
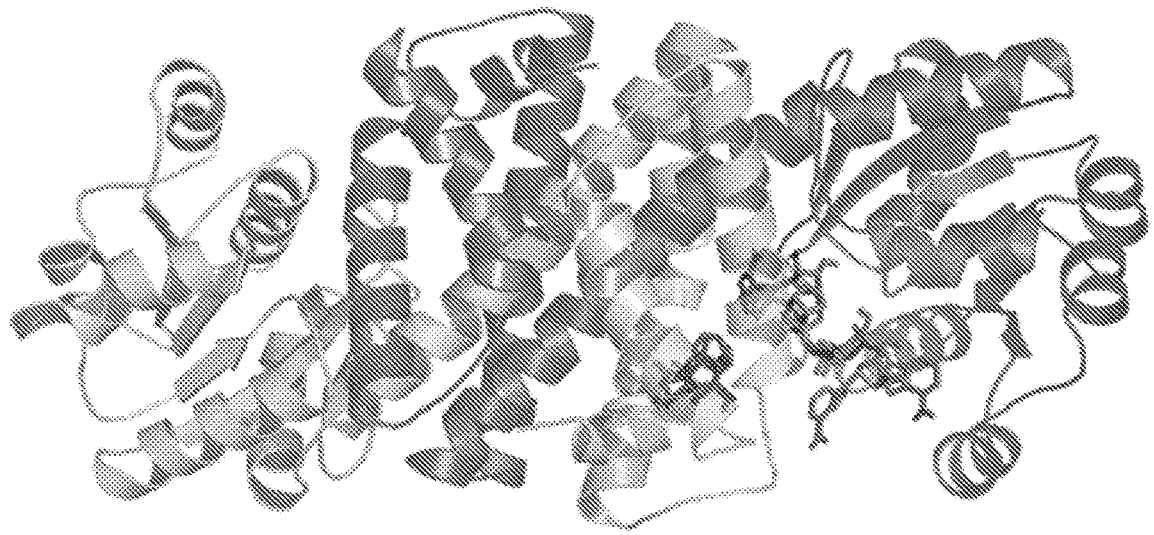
FIG. 2*c* is a simulation diagram of docking between a monomer MesPDH enzyme model Mc and different substrates in Embodiment 2 of the present invention.

As shown in FIGS. 2a-2c, after MEPDH enzyme models Ma, Mb and Mc were docked with four reactant molecules respectively, it was found that myosmine, glucose and gluconic acid were all at similar positions, while NAD+ and NADH were located in another pocket. It was speculated from the model Mb that the MEPDH enzyme was most likely to exert its activity in the form of a dimer, while myosmine, glucose and gluconic acid competed for reduction in the same pocket of a monomer, and NAD+ and NADH competed in the same pocket of another monomer. In the dimer model Mb, the positions of the two substrate pockets of the two monomers were basically the same, indicating that each substrate underwent multiple reduction reactions in this reaction region.

3. Selection of Amino Acid Sites

Based on the foregoing three different models and the results of molecular docking, to enhance the dehydrogenase activity without affecting the imine reduction activity of the enzyme, the mutation sites were selected as amino acids L283 and L286, which were close to glucose and the surface of the enzyme molecule. By mutating leucine into valine, side chain groups of these two amino acids were shortened, the size of substrate active pocket was increased, and the composition of hydrophobic amino acids in the active pocket was not changed.

Embodiment 3

Acquisition of Recombinant Wild Enzyme Strain BL21 (DE3)/pET-32a-MesPDH:

The whole gene was synthesized and optimized by using codon preference of *Escherichia coli* to obtain the MesPDH enzyme gene, with a nucleotide sequence as shown in SEQ ID NO: 4. The gene was ligated to a pET-32a plasmid, and the obtained recombinant plasmid was named pET-32a-MesPDH. The plasmid was transformed into *Escherichia coli* BL21(DE3) and the recombinant strain was named BL21(DE3)/pET-32a-MesPDH. The amino acid sequence of the wild-type MesPDH enzyme expressed by the recombinant wild-type enzyme strain is as shown in SEQ ID NO: 3.

Embodiment 4

Acquisition of MesPDH Mutant Strains:

1. Construction of a Mutant Vector by Full Plasmid PCR (1) Small amount of plasmid extraction of recombinant plasmid pET-32a-MesPDH (2) A mutation primer was designed and had a 15 bp overlap region and 15 bp extension region, and the mutation site was designed in the overlap region. Plasmid pET-32a-MesPDH was used as a template for PCR full plasmid amplification, and a PCR system is shown in Table 1:

TABLE 1

| PCR System | |
|---|---|
| 2 × PrimeSTAR ® Max DNA Polymerase | 25 μL |
| pET-3 2a-MesPDH | 1 μL |
| 283/286-F | 1 μL |
| 283/286-R | 1 μL |
| ddH$_2$O | Add to 50 μL |

The mutation primers include a primer 283/286-F (as shown in SEQ ID NO. 5) and a primer 283/286-R (as shown in SEQ ID NO. 6), and the primer 283/286-F and the primer 283/286-R are a PCR upstream primer and downstream primer designed to simultaneously mutate the 283$^{rd}$ and 286$^{th}$ amino acids into valine. Specific primer information is shown in Table 2.

TABLE 2

| Mutation Primers | | |
|---|---|---|
| Primers | Sequence(5'-3') (mutate gene underlined) | SEQ ID NO. |
| 283/286-F | gat<u>gtt</u>gcaagc<u>gtt</u>gcattactgtttcgtaat | 5 |
| 283/286-R | tgcaac<u>gct</u>tgcaacatcgtcttccatgcttcc | 6 |

A mutant L283V/L286V was prepared by using the primer 283/286-F and the primer 283/286-R and PCR amplification. An amino acid sequence of the mutant L283V/L286V is as shown in SEQ ID NO: 1; and a nucleotide sequence of the gene encoding the mutant L283V/L286V is as shown in SEQ ID NO: 2.

PCR amplification procedure: pre-denaturation was performed at 98° C. for 3 min; and a cycle was set to: denaturing at 98° C. for 10 s, annealing at 62° C. for 15 s, and extending at 72° C. for 2 min; 30 cycles were performed; finally extension was performed at 72° C. for 10 min; and after the reaction, a PCR product was recovered by using a kit.

(3) The template DNA was removed through enzyme digestion, and the PCR product underwent enzyme digestion. An enzyme digestion system is shown in Table 3:

TABLE 3

| QuickCut Dpn I | 1 μL |
|---|---|
| PCR Product | ≤1 μL |
| 10 × QuickCut Buffer | 3 μL |
| ddH$_2$O | Add to 30 μL |

The enzyme digestion system was digested in a metal bath at 37° C. for 1 h, and after the reaction, an enzyme digestion product was recovered by using a kit to obtain a mutant product.

2. Sequencing Verification and Successful Construction of Mutant Strains

The mutant product was transformed into competent cells of *Escherichia coli* BL21(DE3), inverted at 37° C. for overnight culture, quasi-positive transformants were selected for sequencing verification, and mutant expression strains were successfully obtained.

Embodiment 5

Whole Cell Catalytic Reaction of a Dehydrogenase Mutant L283V/L286V

1. Induction of Recombinant Strains of MesPDH and Recombinant Strains of a Mutant and Preparation of a Whole Cell Enzyme Solution (1) BL21(DE3)/pET-32a-MesPDH and BL21(DE3)/pET-32a-L283V/L286V strains were taken, and activated by streaking on an LB plate containing Amp (100 µg/mL). After inverted culture at 37° C. overnight, a single colony was selected and inoculated into 5 mL of LB liquid medium containing Amp, and underwent shaking culture at 37° C. for 12-16 h at 200 r/min. The seed solution cultured overnight was inoculated into 20 mL of fresh LB liquid medium containing Amp based on an inoculation amount of 1%, and underwent shaking culture at 37° C. for 2-3 h at 200 r/min until OD 600 was 0.6-0.8. Then IPTG with a final concentration of 0.5 mM was added, and the culture solution was placed at 20° C. and underwent shaking culture at 200 r/min for 16 h to induce protein expression.

(2) After induction, centrifugation was performed at 4° C. and 6000 rpm for 5 min to collect cells. After the cells were washed with a phosphate buffer (with pH of 7.0) once, an appropriate amount of phosphate buffer (pH 7.0) was added based on a wet weight of the cells to resuspend the cells to obtain a cell suspension with a whole cell concentration of 100 mg/mL. All operations were performed on ice or at 4° C.

2. Whole Cell Reaction (1) The whole cell suspensions of a wild-type MesPDH enzyme and a mutant L283V/L286V enzyme obtained in the foregoing experiments were used as an enzyme solution to test the catalytic reaction of myosmine in groups. Specific reaction systems are shown in Table 4 and Table 5.

TABLE 4

| Reaction System of MesPDH Enzyme or L283V/L286V Enzyme | |
|---|---|
| MesPDH enzyme/ L283 V/L286V enzyme whole cell enzyme solution | 10 mg/mL |
| Myosmine solution | 10 mg/mL |
| Glucose | 18.5 mg/mL |
| Phosphate buffer (pH 7.0) | Add to 1 mL |

TABLE 5

| Reaction System of MesPDH Enzyme or L283V/L286V Enzyme | |
|---|---|
| MesPDH enzyme/L283V/L286V enzyme whole cell enzyme solution | 10 mg/mL |
| Myosmine solution | 10 mg/mL |
| Glucose | 0.5 mg/mL |
| Phosphate buffer (pH 7.0) | Add to 1 mL |

(2) The foregoing reaction system underwent oscillation reaction at 30° C. for 24 h at a rotation speed of 200 rpm. After the reaction was finished, absolute ethanol twice the volume of the reaction solution was added to the reaction solution to stop the reaction, and then the reaction mixture underwent rotary evaporation at 65° C. and 100 rpm to remove the solvent. Finally, 2 mL of absolute ethanol was added to redissolve a product after the rotary evaporation, the solution was filtered by a 0.45 µm organic filter, and then detection by using an HPLC was performed.

3. S-Nornicotine Detection Method

Qualitative and quantitative analysis of S-nornicotine was performed on reaction results of the reaction systems in Table 4 and Table 5 by using the HPLC, and chromatographic conditions were as follows:

High performance liquid chromatograph: Agilent 1100 Series
  Chromatographic column: ChiralpakAD-Hcolumn (250 mm×4.6 mm×5 µm)
  Detector: DAD detector, with a detection wavelength of 254 nm
  Mobile phase ratio and elution conditions: flow rate of 1 mL/min; column temperature of 30° C.; an injection volume of 10 µL; and an isocratic elution mobile phase system being n-hexane:ethanol:ethylenediamine=74.9:25.0:0.1.

4. Result Analysis

Figure 3:
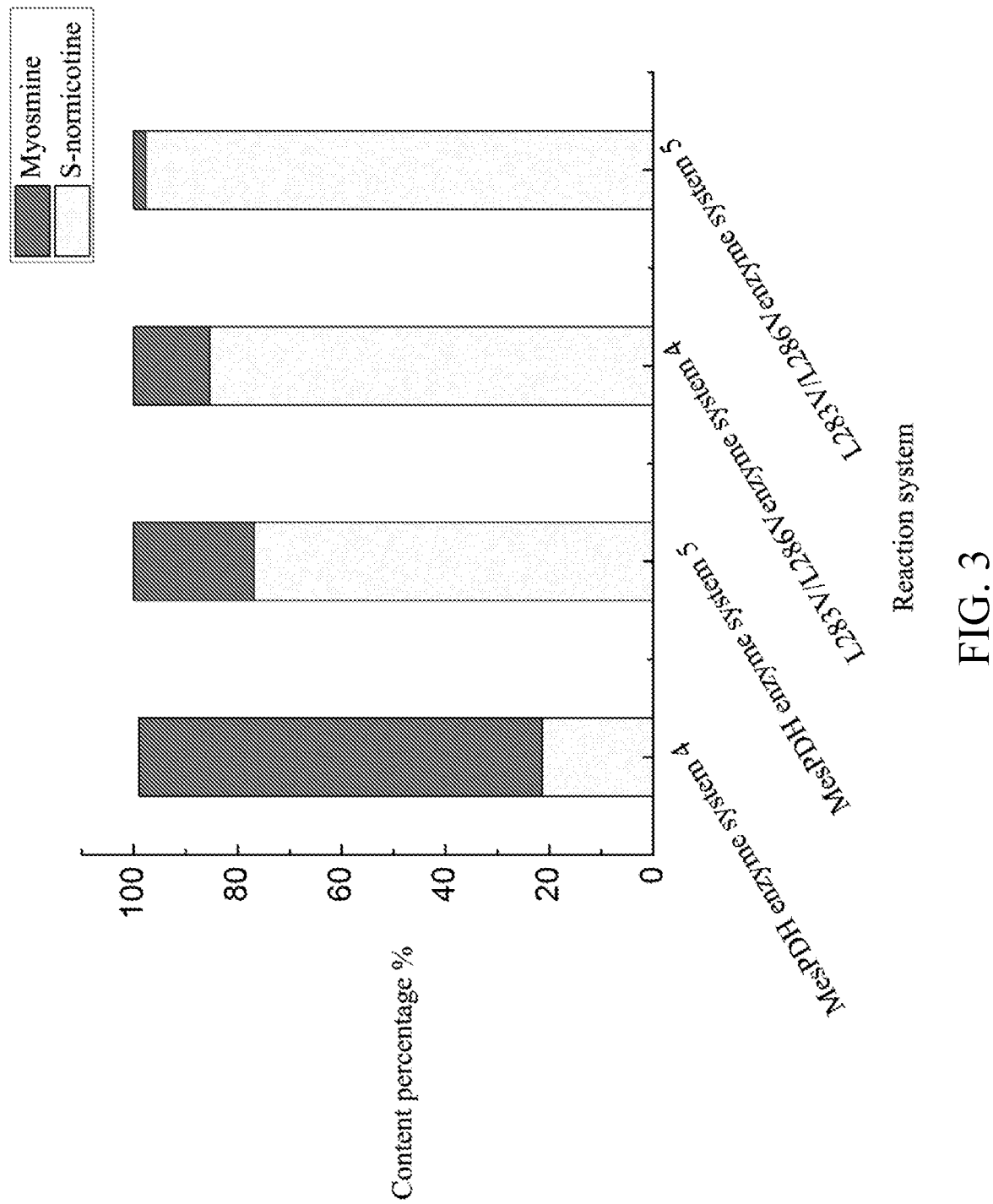
FIG. 3 is a comparison diagram of content of myosmine and S-nornicotine after the reaction of each whole-cell catalytic system in Embodiment 5 of the present invention.

As shown in FIG. 3, a comparison diagram of content of myosmine and S-nornicotine after the reaction of each whole-cell catalytic system shows that when the wild-type MesPDH enzyme was used for the whole-cell catalytic reaction of the system in Table 4, after reaction for 24 h, the content of components in the reaction system was detected, and 80% of myosmine remained, indicating that the reaction efficiency was low, and a large amount of myosmine still did not participate in the reaction; however, when the whole-cell catalytic reaction of the system in Table 5 was performed, the content of components in the reaction system was detected after reaction for 24 h, 25% of the myosmine remained, and the residue of myosmine was reduced, indicating that the reaction efficiency was improved after glucose dehydrogenase (GDH commercial enzyme) was supplemented in the system. The results showed that the activity of glucose dehydrogenase of the wild-type MesPDH enzyme was relatively low, so that it was required to supplement glucose dehydrogenase to improve the reaction efficiency.

In addition, when the mutant L283V/L286V enzyme was used for the whole-cell catalysis of the system in Table 4, the content of components in the reaction system was detected after reaction for 24 h, less than 20% of myosmine remained, and most of the myosmine was transformed into S-nornicotine. When the whole-cell catalytic reaction of the system in Table 5 was performed, almost no myosmine remained, and the reaction could completely transform the myosmine into S-nornicotine, indicating that the mutant L283V/L286V enzyme improved its dehydrogenase activity, while not affecting the reductase activity, and could complete high transformation without additional glucose dehydrogenase.

Figure 4:
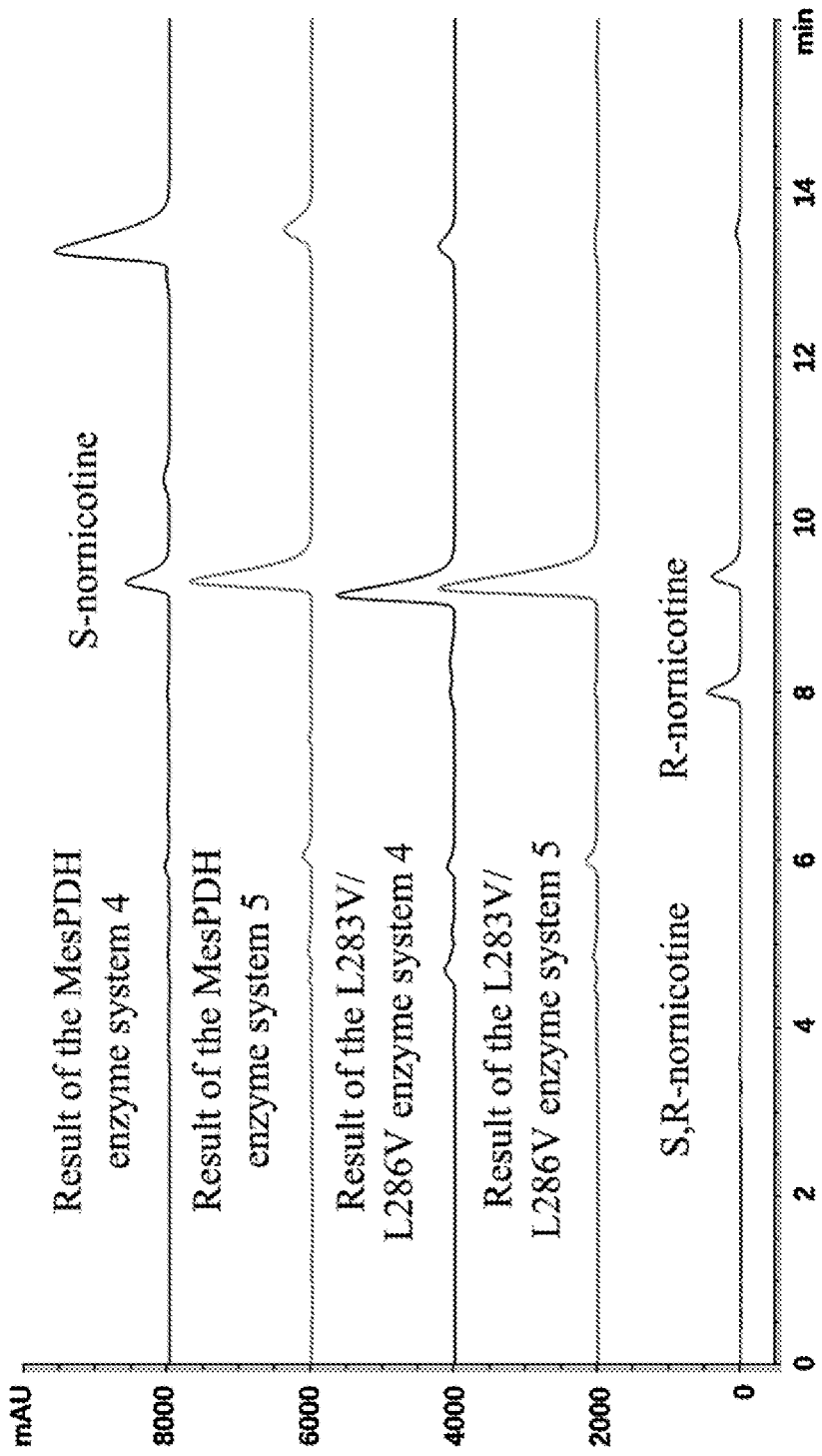
FIG. 4 is a liquid phase detection diagram of each reaction system in Embodiment 5 of the present invention.

Liquid phase detection results are shown in FIG. 4. The peak time of R-nornicotine was about 7.98 min, the peak time of S-nornicotine was about 9.32 min, and the peak time of myosmine was about 13.42 min. Nornicotine produced by all reactions was S-nornicotine, and no R-nornicotine was generated. The optical purity of the product was extremely high.

Figure 5:
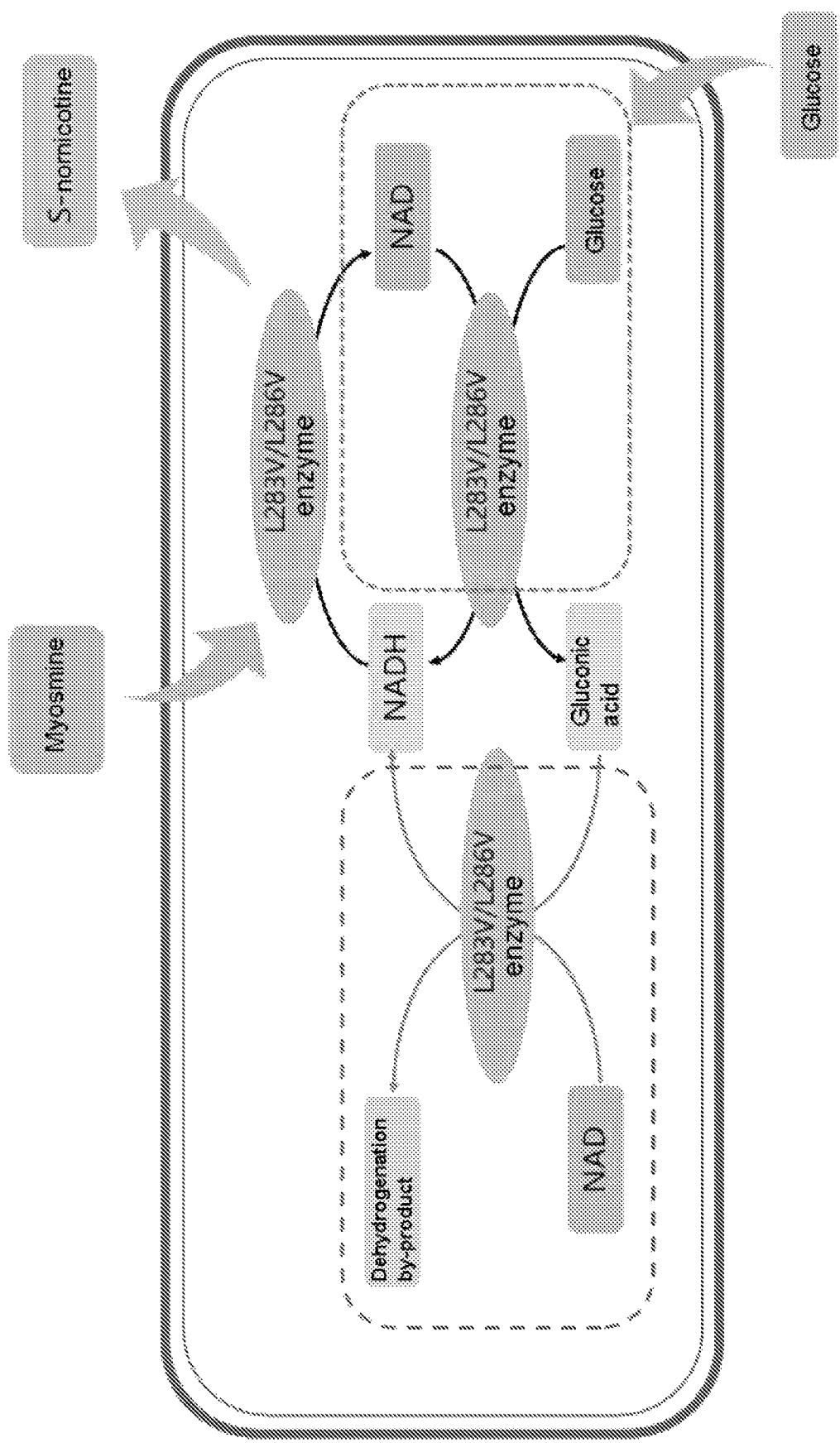
FIG. 5 is a reaction flowchart of a whole-cell catalytic synthesis system in Embodiment 5 of the present invention.

The process of whole cell synthesis of S-nornicotine is shown in FIG. 5. The mutant L283V/L286V played the role of imine reductase and two-step dehydrogenase in the whole cell catalysis, and could efficiently transform the myosmine into S-nornicotine by combining with exogenous glucose and NAD supply from the whole cell.

The foregoing descriptions are merely preferred implementations of the present invention. It should be noted that a person of ordinary skill in the art may further make several improvements and modifications without departing from the principle of the present invention, and such improvements and modifications should be deemed as falling within the protection scope of the present invention.

What is claimed is:

1. A dehydrogenase mutant comprising the amino acid sequence as shown in SEQ ID NO: 1.

2. A nucleic acid encoding the dehydrogenase mutant according to claim 1, wherein the nucleic acid comprises a nucleotide sequence comprising SEQ ID NO: 2.

3. A method for preparing the dehydrogenase mutant according to claim 1, comprising the following steps:

S1: ligating a starting gene encoding a *Mesorhizobium* 6-phosphoglycerate dehydrogenase (MesPDH) enzyme into a plasmid to obtain a recombinant plasmid, wherein the MesPDH enzyme comprises the amino acid sequence as shown in SEQ ID NO: 3;

S2: performing PCR amplification to produce a mutant gene as a product by contacting two mutation primers with the recombinant plasmid as a template, wherein PCR amplification results in the mutant gene encoding SEQ ID NO: 1 so that $283^{rd}$ and $286^{th}$ amino acids of SEQ ID NO: 3 encoded by the starting gene are both simultaneously mutated to encode valine, and recovering the mutant gene; and S3: transforming the mutant gene into a host cell, culturing the host cell, and inducing expression of the mutant gene in the host cell to obtain the dehydrogenase mutant.

4. The preparation method according to claim 3, wherein a nucleotide sequence of the starting gene encoding the MesPDH enzyme comprises the nucleotide sequence as shown in SEQ ID NO: 4.

5. The preparation method according to claim 3, wherein the two mutation primers comprise a primer 283/286-F and a primer 283/286-R; wherein the primer 283/286-F comprises the nucleotide sequence as shown in SEQ ID NO: 5, and the primer 283/286-R comprises the nucleotide sequence as shown in SEQ ID NO: 6.

6. The preparation method according to claim 3, wherein the host cell is *Escherichia coli*.

7. The preparation method according to claim 3, wherein in step S2 PCR amplification comprises performing pre-denaturation at 98° C. for 3 min; and then performing 30 cycles of denaturing at 98° C. for 10 s, annealing at 62° C. for 15 s, and extending at 72° C. for 2 min; and after the 30 cycles, performing extension at 72° C. for 10 min.

8. A method for preparing (S)-nornicotine, comprising:
contacting an *Escherichia coli* whole cell containing a dehydrogenase mutant according to claim 1 with myosmine and glucose to produce (S)-nornicotine.

* * * * *